United States Patent [19]

Ramanarayanan et al.

[11] Patent Number: 5,464,523
[45] Date of Patent: Nov. 7, 1995

[54] SENSORS FOR SULFUR ACTIVITY MEASUREMENTS

[75] Inventors: Trikur A. Ramanarayanan, Somerset; Vinod K. Pareek, Flemington; James D. Mumford, III, Long Valley; Horst Witzke, Flemington, all of N.J.

[73] Assignee: Exxon Research & Engineering Co., Florham Park, N.J.

[21] Appl. No.: 245,341

[22] Filed: May 18, 1994

Related U.S. Application Data

[63] Continuation-in-part of Ser. No. 64,262, May 20, 1993, abandoned.

[51] Int. Cl.$^6$ .......................... G01N 27/26; G01N 27/407
[52] U.S. Cl. .................. 204/424; 204/153.1; 204/400; 204/421; 204/429; 422/98
[58] Field of Search .................. 204/153.1, 416, 204/419, 153.18, 400, 421–429; 422/98; 429/30, 33, 191, 193

[56] References Cited

U.S. PATENT DOCUMENTS

| | | | |
|---|---|---|---|
| 3,437,446 | 4/1968 | Pierce | 422/98 |
| 3,558,280 | 1/1971 | Panson et al. | 422/98 |
| 4,406,754 | 9/1983 | Narita et al. | 204/424 |
| 4,507,643 | 3/1985 | Sunano et al. | 422/98 |
| 4,885,929 | 12/1989 | Kasahara et al. | 422/98 |
| 5,082,789 | 1/1992 | Morrison et al. | 422/98 |

OTHER PUBLICATIONS

Noddack et al., "The Electrochemical Series of the Sulfides", Z. Electrochem., vol. 59, (1955), pp. 752–755.

*Primary Examiner*—T. Tung
*Attorney, Agent, or Firm*—Ronald D. Hantman

[57] ABSTRACT

A method and a sensor to measure the sulfur activity in sulfur-containing environments are disclosed. The active component is a non-stoichiometric metal sulfide foil or film. In the case of a thin sulfide film, a ceramic substrate is employed for improved mechanical rigidity. The electrical conductivity of the sulfide is related to the sulfur activity of the process stream to which it is exposed.

6 Claims, 3 Drawing Sheets

SENSORS FOR SULFUR ACTIVITY MEASUREMENTS

CROSS-REFERENCE TO RELATED APPLICATIONS

This application is a Continuation-in-Part of U.S. Ser. No. 064,262 filed May 20, 1993, (which is based on PM 92CL-039 and communications from inventors), now abandoned.

BACKGROUND OF THE INVENTION

The present invention relates to measuring the thermodynamic sulfur activity in a process environment. In particular, the present invention includes a method and a sensor to measure sulfur activity.

In many processes, for example in the refining of crudes or in sour gas production wells, there is a significant need to measure the thermodynamic activity of sulfur which is established in the environment by the interplay of the various sulfur containing corrosive species. Sulfur activity is a well known measure of the available sulfur for reaction (see e.g., "An Analysis of the Phase Equilibria in the Fe-FeS System", *Metallurgical Transactions B*, p. 37–41, Vol. 6B, March 1975). To provide operational flexibility in these environments, it is of great interest to predict the rates of corrosion. Typically, these environments exhibit temperature ranges 150° F. to 1000° F. The thermodynamic activity of sulfur can be used as a generalized index of corrosivity. Thus, if the sulfur activity can be directly measured by means of a sensor, this will provide a determination of corrosivity prediction.

SUMMARY OF THE INVENTION

The present invention includes a method and a device to determine the sulfur activity in a given environment (such as a feedstream). This activity can be related to the sulfur concentration in the environment.

The sensor includes several elements: a non-stoichiometric sulfide, $M_{\alpha-x}S$, whose conductivity varies with sulfur activity where the maximum value of x is between 0.002 and 0.5; electrodes attached to the sulfide; and a means for measuring the conductivity of said sulfide and correlating the electrical conductivity with the sulfur activity.

In a preferred embodiment, the sulfide is iron sulfide (pyrrhotite) or cuprous sulfide.

The sensor is placed in an environment whose sulfur activity is to be determined. The conductivity and hence, resistivity of the sulfide is measured. The corresponding sulfur activity and sulfur concentration may then be determined from a calibration curve of the conductivity (or resistivity) vs. sulfur activity.

DESCRIPTION OF THE PREFERRED EMBODIMENT

The present invention includes a method and a device to determine the sulfur activity in a given environment (such as a feed stream) at a temperature which will be limited to below 1000° F. for such applications. One of the elements of the device is a non-stoichiometric metal sulfide $M_{\alpha-x}S$ whose metal to sulfur ratio ($\alpha$-x) varies over a wide range and whose conductivity varies with sulfur activity. The measurement of conductivity variation is made possible by the rapid diffusion of metal ions in these non-stoichiometric sulfides. The non-stoichiometry of the binary sulfide $M_{\alpha-x}S$ is defined by the deviation, x of the M/S ratio from the stoichiometric constant, $\alpha$. $\alpha$ is defined as the metal to sulfur ratio in the binary sulfide when there is no deviation from stoichiometry. For the sulfides of the present invention, the maximum value of x ($x_{max}$) is in the range $0.002 < x_{max} < 0.5$. In a preferred embodiment, $x_{max}$ is in the range $0.02 < x_{max} < 0.5$. Examples of sulfides of our invention are $Cu_{2-x}S$ ($x_{max}=0.23$), $Fe_{1-x}S$ ($x_{max}=0.25$). The larger non-stoichiometry range allows rapid atomic diffusion in the temperature range (below 1000° F.) where sensors are used. The non-stoichiometry of the sulfides is due to the metal deficiency on the cation lattice while the anion lattice is nearly perfect. The sensor also includes electrodes attached to the sulfide and a means for measuring the electrical conductivity of the said sulfide and correlating the conductivity with the sulfur activity.

The sensor includes a non-stoichiometric sulfide which in general is a p-type or n-type semi-conductor. The presence of metal vacancies balanced by electron holes provides semi conduction in the former case while metal interstitials balanced by excess electrons causes semi conduction in the latter case. The measured total conductivity is essentially equal to the p-type or the n-type conductivity which is proportional to the metal deficit or metal excess of the sulfide, which in turn is directly related to the sulfur chemical potential or activity of the environment. Metal sulfides useful in the present invention include $Cu_{2-x}S$, $Fe_{1-x}S$, $Co_{1-x}S$, $Ni_3S_{2\pm x}$.

One method of practicing this invention is to prepare thin self supporting foils of the non-stoichiometric sulfide sensor and use four probe d.c. techniques to measure its electrical conductivity. This can be done by first starting with a metal foil to which inert metal electrodes are spot welded. The foil/electrode assembly is then exposed to a controlled sulfur environment whereby the metal foil is converted to the non-stoichiometric sulfide sensor element. The sensor is then ready for placement in the process stream. The steady state conductivity of the foil provides a measure of the sulfur activity of the stream.

Figure 1:
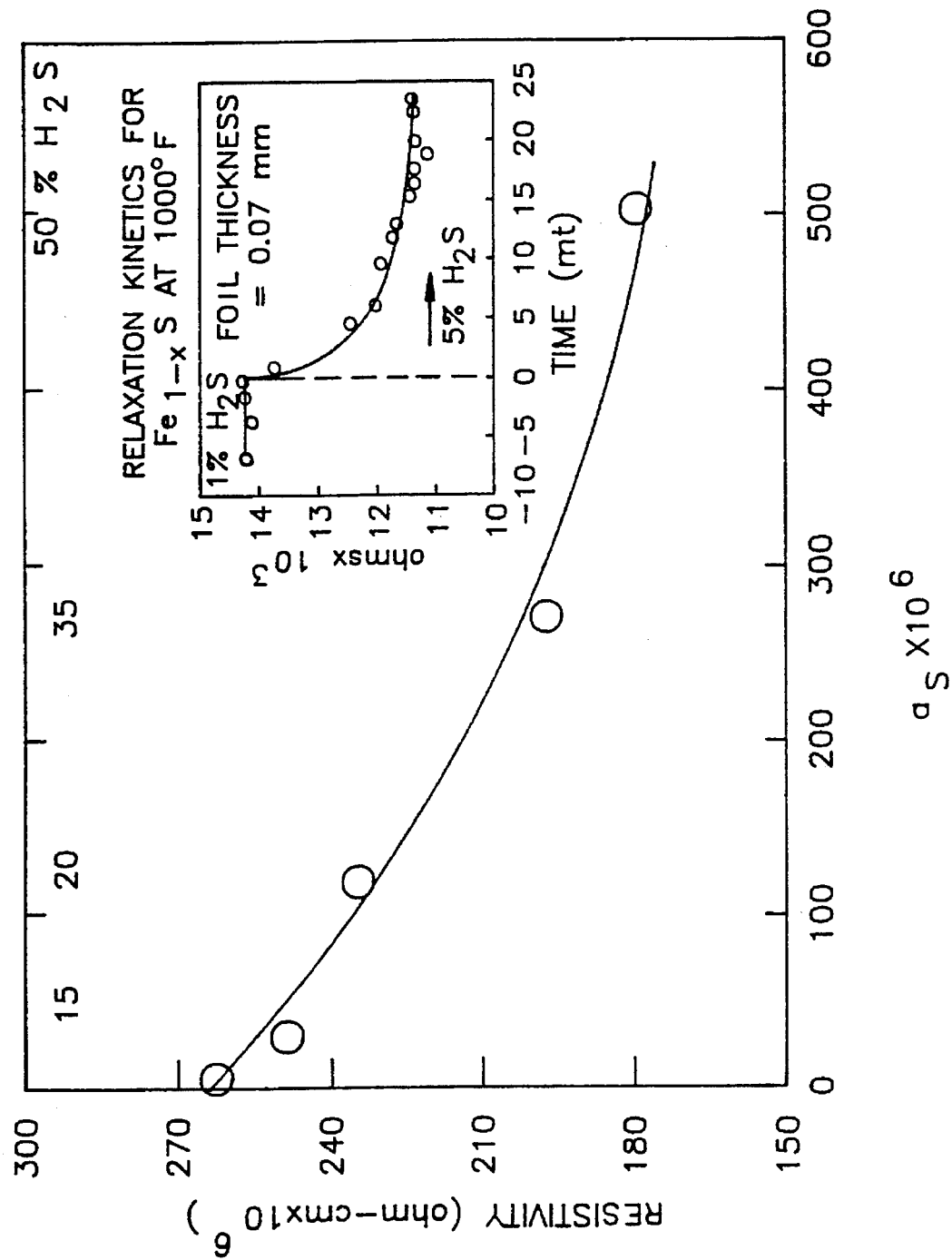
FIG. 1 shows the resistivity (inverse of conductivity) of a cuprous sulfide foil as a function of the sulfur activity at 1000° F. The sulfur activity was established using equilibrated $H_2S/H_2$ mixtures.
Figure 2:
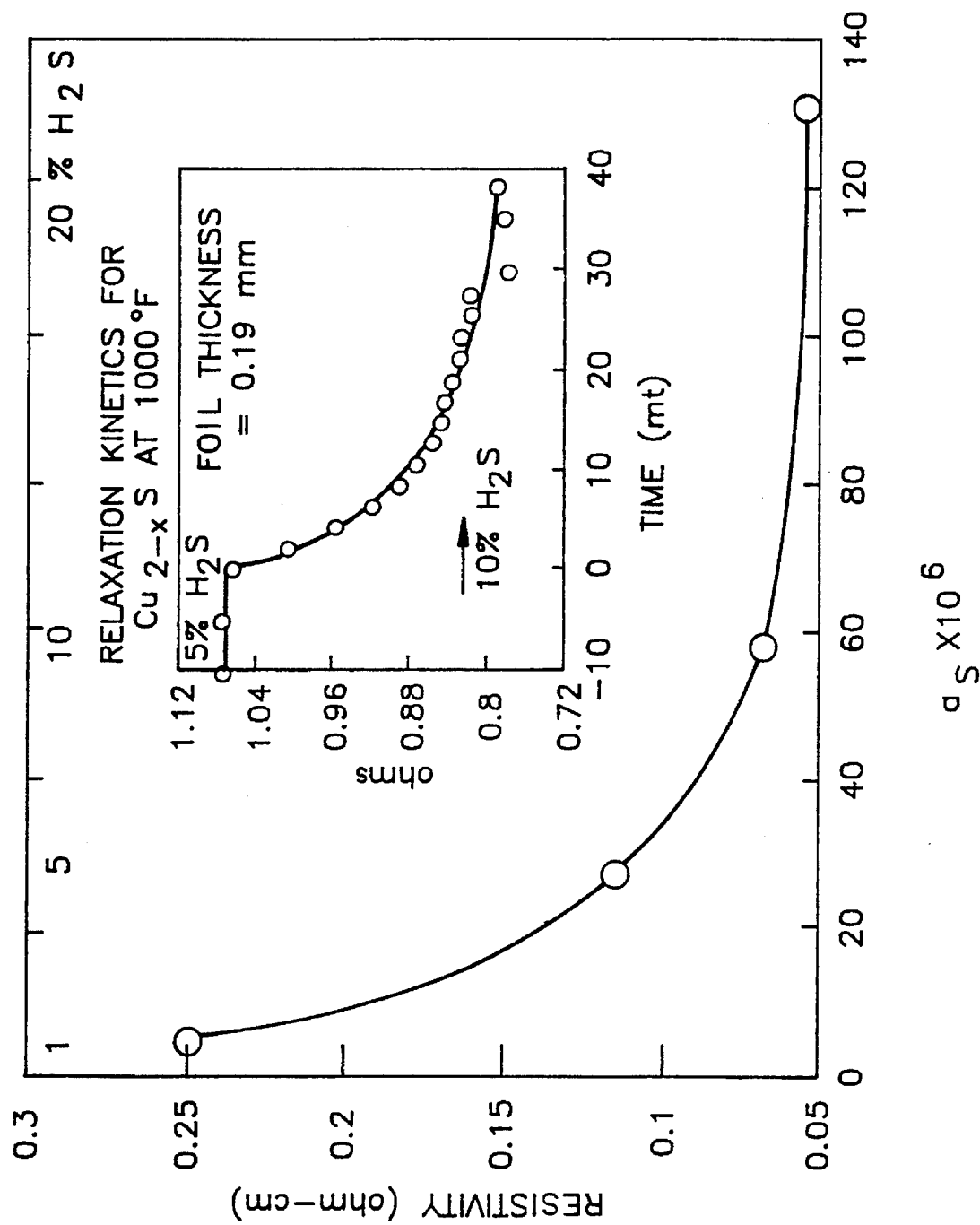
FIG. 2 shows the resistivity (inverse of conductivity) of an iron sulfide foil as a function of the sulfur activity in the $H_2S/H_2$ mixture at 1000° F.

The sulfur activity-conductivity relationship for the sulfur sensors may be determined by using iron foils and copper foils in $H_2S/H_2$ mixtures of known sulfur activity. The foils convert to the corresponding sulfides. FIGS. 1 and 2 show the resistivity (inverse of conductivity) of cuprous sulfide and iron sulfide foils respectively as a function of the sulfur activity in the $H_2S/H_2$ mixture at 1000° F. These figures serve as a calibration plot of conductivity vs. sulfur activity. Shown in the inset relaxation curves of the variation of resistivity with time when the environment is changed from one sulfur content to another. This provides a measure of the response time of the sensor at 1000° F.

Figure 3:
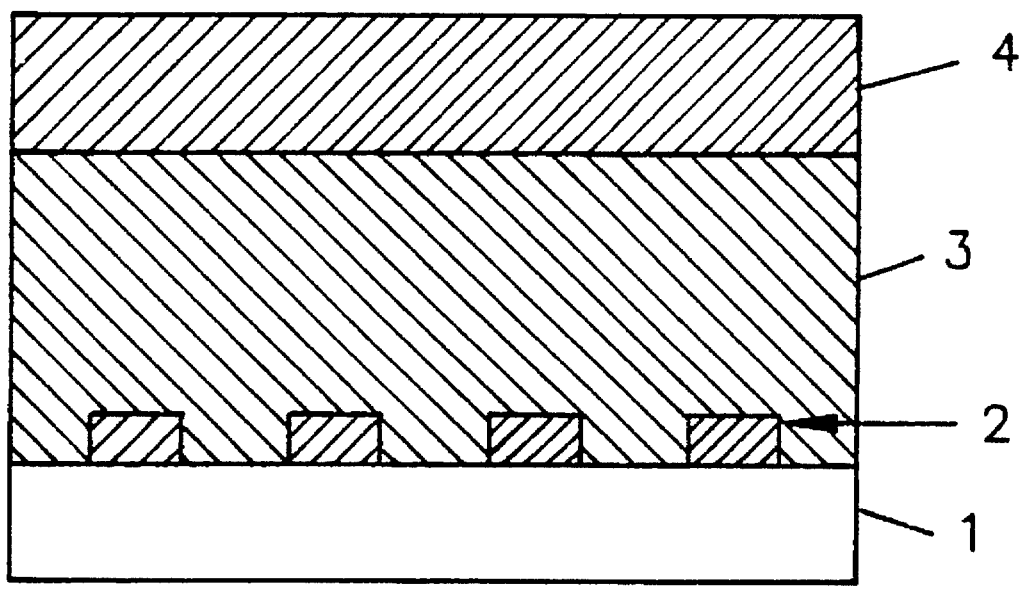
FIG. 3 shows a schematic diagram of an embodiment the sensor of the present invention.

The sensor may be made more durable by replacing the sulfide foils with thin sulfide films deposited on a non-conductive ceramic substrate (see FIG. 3). This will provide for enhanced mechanical integrity as well as faster response times. A suitable substrate (1) could be a ceramic wafer with conductive electrodes (2) formed by thin or thick film techniques which are well known in the art. One method of practicing this invention is to deposit a thin film of the metal by sputtering or evaporation and subsequently converting the metal film into a sulfide (3). Another technique could be to deposit the metal sulfide layer in a single step by reactive sputter deposition. Such thin film deposition techniques are also well known in the art.

In many process streams, erosive damage of sensor components can occur because of particulate and velocity effects. The sensor of the present invention may include an erosion resistant porous ceramic layer (4) between the sensor and the process stream. Such a membrane layer could be formed by solgel techniques, for example.

What is claimed is:

1. A sensor for determining the sulfur activity in an environment comprising:

(a) a non-stoichiometric semi-conducting metal sulfide, $M_{\alpha-x}S$, whose p-type or n-type conductivity varies with sulfur activity, where M is the metal and $\alpha$ is the stoichiometric constant, and x is the deviation from that constant and where the maximum value of x is between 0.002 and 0.5;

(b) electrodes attached to said sulfide; and (c) means for measuring the p-type or n-type conductivity of said sulfide and correlating said conductivity with the sulfur activity.

2. The sensor of claim 1 wherein said sulfide is iron sulfide or copper sulfide.

3. The sensor of claim 1 wherein said sulfide is a thin self supporting foil.

4. The sensor of claim 1 wherein said sulfide is a thin film deposited on a substrate.

5. The sensor of claim 4 wherein said substrate is a ceramic material.

6. The sensor of claim 4 further comprising a porous, corrosion and erosion resistant layer between said sulfide and said environment.

* * * * *